US012714823B2

(12) United States Patent
Motose et al.

(10) Patent No.: US 12,714,823 B2
(45) Date of Patent: Aug. 25, 2026

(54) CATHETER

(71) Applicant: TERUMO KABUSHIKI KAISHA, Tokyo (JP)

(72) Inventors: Yuji Motose, Kanagawa (JP); Daisuke Shimada, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 834 days.

(21) Appl. No.: 18/057,313

(22) Filed: Nov. 21, 2022

(65) Prior Publication Data

US 2023/0089179 A1 Mar. 23, 2023

Related U.S. Application Data

(63) Continuation of application No. PCT/JP2021/012979, filed on Mar. 26, 2021.

(30) Foreign Application Priority Data

Jun. 1, 2020 (JP) ................................ 2020-095665

(51) Int. Cl.
*A61M 25/00* (2006.01)

(52) U.S. Cl.
CPC .... *A61M 25/0014* (2013.01); *A61M 25/0067* (2013.01); *A61M 2025/0058* (2013.01); *A61M 2025/0098* (2013.01)

(58) Field of Classification Search
CPC .......... A61M 25/0014; A61M 25/0067; A61M 2025/0058; A61M 2025/0098
See application file for complete search history.

(56) References Cited

U.S. PATENT DOCUMENTS 4,664,115 A * 5/1987 Ohachi ................. C08F 259/04 606/1
4,802,947 A 2/1989 Bartholomew
(Continued)

FOREIGN PATENT DOCUMENTS

JP S6317486 U 2/1988
JP H10180802 A 7/1998
(Continued)

OTHER PUBLICATIONS

The extended European Search Report issued Oct. 20, 2023, by the European Patent Office in corresponding European Patent Application No. 21818778.9-1122. (8 pages).
(Continued)

*Primary Examiner* — Edelmira Bosques
(74) *Attorney, Agent, or Firm* — BUCHANAN INGERSOLL & ROONEY PC

(57) ABSTRACT

A catheter is capable of firmly fixing a shaft and a hub, and preventing a decrease in dimensional accuracy of an outer side of the hub in a radial direction. The catheter includes: a shaft that is a tubular body in which a lumen extending the shaft from a distal end to a proximal end is formed, and that includes a shaft proximal surface in which the lumen is opened and a shaft outer surface that is an outer peripheral surface of the tubular body; and a hub that is attached to the proximal end of the shaft. The hub includes a tubular accommodation unit configured to accommodate the shaft, the accommodation unit includes a hub melted surface that is directly welded to the shaft outer surface, and an absolute value of a residual strain of the accommodation unit decreases outward in a radial direction from the hub melted surface.

21 Claims, 3 Drawing Sheets

(56) References Cited

U.S. PATENT DOCUMENTS

| | | | |
|---|---|---|---|
| 8,353,876 | B2 | 1/2013 | Suwito et al. |
| 2009/0157007 | A1 | 6/2009 | McKinnon |
| 2009/0192496 | A1 | 7/2009 | Suwito et al. |
| 2011/0139754 | A1 | 6/2011 | Romanowski et al. |
| 2014/0328565 | A1 | 11/2014 | Sakabe et al. |
| 2017/0340860 | A1 | 11/2017 | Eberhardt et al. |
| 2019/0255282 | A1 | 8/2019 | Inukai et al. |
| 2023/0078719 | A1 | 3/2023 | Motose et al. |

FOREIGN PATENT DOCUMENTS

| | | | |
|---|---|---|---|
| WO | 2014103599 | A1 | 7/2014 |
| WO | 2016/092208 | A1 | 6/2016 |

OTHER PUBLICATIONS

English Translations of the International Search Report (Form PCT/ISA/210) and the Written Opinion of the International Searching Authority (Form PCT/ISA/237) issued May 25, 2021, by the Japan Patent Office in corresponding International Application No. PCT/JP2021/012979. (8 pages).

International Search Report (PCT/ISA/210) with translation and Written Opinion (PCT/ISA/237) mailed on May 25, 2021, by the Japan Patent Office as the International Searching Authority for International Application No. PCT/JP2021/012979. (10 pages).

U.S. Appl. No. 18/057,258, filed Nov. 21, 2022, Yuji Motose et al.

First Office Action issued on Jun. 27, 2024, by the China National Intellectual Property Administration in corresponding Chinese Patent Application No. 202180038126.6 and an English translation of the Action. (10 pages).

* cited by examiner 40 41 L H 25 20 26

49 28 29 30 46 50

40 41 L H 25 20 26

49 28 29 30 46 50

CATHETER

CROSS-REFERENCES TO RELATED APPLICATIONS

This application is a continuation of International Application No. PCT/JP2021/012979 filed on Mar. 26, 2021, which claims priority to Japanese Patent Application No. 2020-095665 filed on Jun. 1, 2020, the entire content of both of which is incorporated herein by reference.

TECHNOLOGICAL FIELD

The present invention generally relates to a catheter.

BACKGROUND DISCUSSION

In recent years, treatment of the inside of a lumen such as a blood vessel by using a catheter has been actively performed since surgical invasiveness is very low. The catheter generally includes a shaft including a lumen extending the shaft from a distal end to a proximal end, and a hub disposed at the proximal end of the shaft. The hub is formed with a passage communicating with the lumen in order to connect to a syringe or the like.

As a method for fixing the proximal end of the shaft to the hub, an insert molding method, a bonding method using an adhesive, and the like are known.

SUMMARY

In an insert molding method described in Japanese Patent Application Publication No. 10-180802 (JP-A-H10-180802), a shaft is disposed in an injection mold, a part of the shaft is pressed by a fixing pin, and a resin for a hub is injection-molded at a high temperature and a high pressure. Therefore, deformation of the shaft caused by the fixing pin or displacement of the shaft in a longitudinal axis direction may occur. The deformation of the shaft and the displacement in the axial center direction may cause a decrease in fixing strength between the shaft and the hub.

In addition, in a bonding method using an adhesive described in Japanese Utility Model Publication No. 63-17486 (JP-UM-B-S63-17486), if a gap between an outer diameter of a shaft and a lumen of a shaft accommodation unit of a hub is excessively small, the adhesive cannot flow therein, and the gap remains between the hub and the shaft, which may cause a decrease in fixing strength between the shaft and the hub. On the other hand, when the gap between the outer diameter of the shaft and the lumen of the shaft accommodation unit of the hub is excessively large, it is difficult to completely fill the gap between the hub and the shaft with the adhesive, and thus the fixing strength between the shaft and the hub may decrease.

The catheter disclosed here is capable of firmly fixing a shaft and a hub and preventing a decrease in dimensional accuracy of an outer side of the hub in a radial direction.

A catheter disclosed here includes: a shaft that is a tubular body in which a lumen extending through the shaft from a distal end to a proximal end is formed, and that includes a shaft proximal surface in which the lumen is opened and a shaft outer surface that is an outer peripheral surface of the tubular body; and a hub that is attached to the proximal end of the shaft. The hub includes a tubular accommodation unit that is configured to accommodate the shaft, the accommodation unit includes a hub melted surface that is directly welded to the shaft outer surface, and an absolute value of a residual strain of the accommodation unit decreases from the hub melted surface outward in a radial direction.

In the catheter configured as described above, since the absolute value of the residual strain of the accommodation unit caused by welding decreases from the hub melted surface outward in the radial direction, the shaft and the hub can be firmly fixed and firmly welded, and thus a decrease in dimensional accuracy of an outer side of the hub in the radial direction can be prevented.

A contour line of the absolute value of the residual strain of the accommodation unit in a cross section passing through a longitudinal axis of the accommodation unit may be formed in an arc shape protruding outward in the radial direction. Accordingly, the absolute value of the residual strain gradually decreases from a portion of the hub melted surface where the absolute value is largest toward two directions, namely an outward direction in the radial direction and the longitudinal axis direction (a distal direction and a proximal direction). Therefore, occurrence of shape distortion of the accommodation unit can be effectively prevented.

The shaft proximal surface may be welded to the hub. Accordingly, the shaft and the hub can be fixed more firmly.

A hub separated surface that is separated outward in the radial direction from the shaft outer surface and faces the shaft outer surface may be formed on a distal side of the accommodation unit. Accordingly, since the shaft is easily bent on an inner side of the distal end of the accommodation unit, stress concentration on the shaft can be prevented, and damage to the shaft can be prevented. In addition, since the shaft is easily bent on the inner side of the distal end of the accommodation unit, when the shaft is bent, it is possible to prevent a force that peels off the shaft from the hub melted surface of the accommodation unit from acting thereon, and thus the fixation of the shaft and the hub can be effectively maintained.

According to another aspect, a catheter comprises: a shaft and a hub. The shaft possesses a distal end and a proximal end, and the shaft is a tubular body that includes a lumen extending from the distal end of the shaft to the proximal end of the shaft. The shaft includes a shaft proximal end surface at the proximal end of the shaft, and the lumen opens to the shaft proximal end surface at the proximal end of the shaft. The shaft also possesses a shaft outer surface and includes a proximal portion, with the proximal portion of the shaft including a radially outer portion and a radially inner portion that both extend along an axial extent of the proximal portion of the shaft, and the radially inner portion of the proximal portion of the shaft is radially inward of the radially outer portion of the proximal portion of the shaft. The hub includes an accommodation unit in which is positioned the proximal portion of the shaft, and the radially outer portion of the proximal portion of the shaft is comprised of a resin that absorbs electromagnetic waves or does not transmit electromagnetic waves. The accommodation unit includes a hub melted surface that is directly welded to the shaft outer surface of the proximal portion of the shaft so that the accommodation unit and the shaft outer surface are welded to one another. The accommodation unit includes a distal-most portion possessing an inner surface that faces the shaft outer surface and is spaced from and not welded to the shaft outer surface so that a gap exists between the inner surface of the accommodation unit and the shaft outer surface.

In accordance with another aspect, a method of securing a shaft of a catheter to a hub of the catheter comprises positioning a proximal portion of the shaft in an accommodation unit of the hub, with the accommodation unit of the hub being a distal portion of the hub, and the accommodation unit of the hub possessing an inner surface and a distal end portion. The proximal portion of the shaft possess a shaft outer surface, and the positioning of the proximal portion of the shaft in the accommodation unit of the hub comprises positioning the proximal portion of the shaft in the accommodation unit of the hub so that the inner surface of the accommodation unit of the hub faces the shaft outer surface of the proximal portion of the shaft. The method additionally comprises heating the shaft outer surface of the proximal portion of the shaft so that the shaft outer surface of the proximal portion of the shaft is heated and melted, and transferring the heat of the shaft outer surface of the proximal portion of the shaft to the inner surface of the accommodation unit to melt at least a part of the inner surface of the accommodation unit to weld the part of the inner surface of the accommodation unit and the shaft proximal side outer surface at a welded surface. An absolute value of a residual strain of the accommodation unit of the hub decreases outward in a radial direction from the welded surface.

BRIEF DESCRIPTION OF THE DRAWINGS

FIGS. 5A and 5B are longitudinal cross-sectional views illustrating a process of welding the shaft to the hub, in which FIG. 5A illustrates a state in which welding is started, and FIG. 5B illustrates a state in which welding is in progress.

FIG. 6 is a longitudinal cross-sectional view illustrating residual strain of the distal portion of the hub and the proximal portion of the shaft with contour lines.

DETAILED DESCRIPTION

Set forth below with reference to the accompanying drawings is a detailed description of an embodiment of a catheter representing an example of the new catheter disclosed here. The dimensions or scales on the drawings may be exaggerated or different from actuality/reality for convenience of description and illustration. In the following description, a side on which a catheter is operated is referred to as a "proximal side", and a side to be inserted into a living body is referred to as a "distal side".

Figure 1:
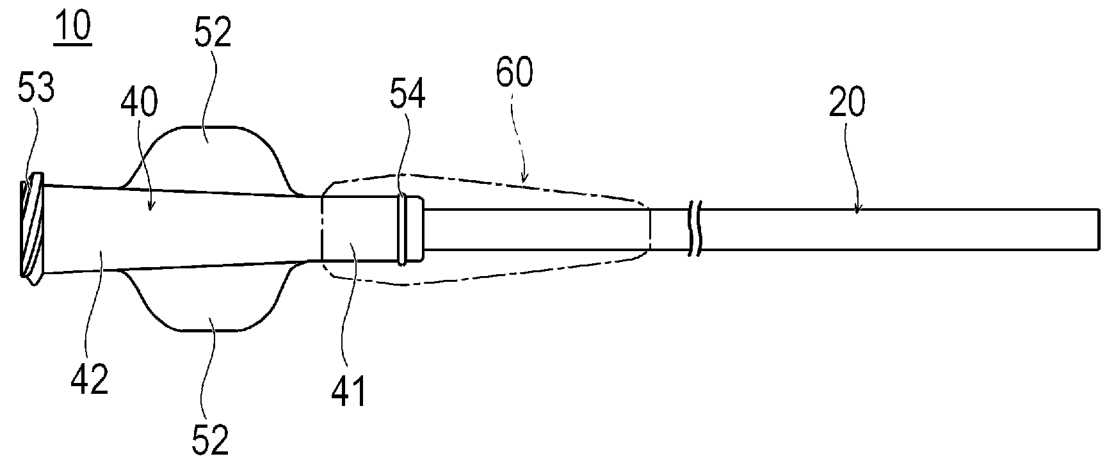
FIG. 1 is a plan view illustrating a catheter according to an embodiment.
Figure 2:
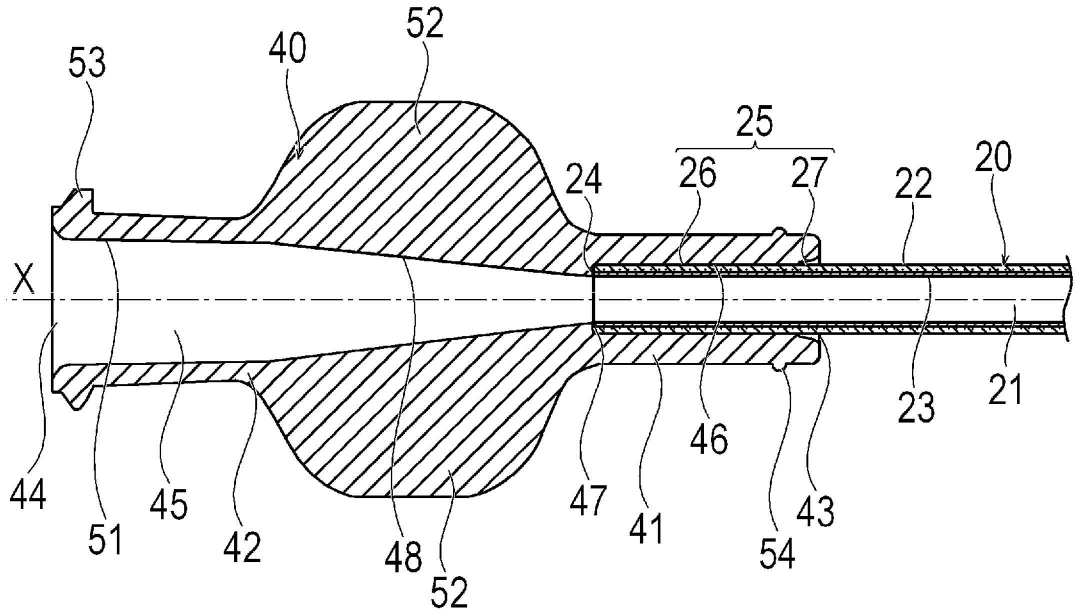
FIG. 2 is a longitudinal cross-sectional view illustrating a hub and a proximal portion of a shaft.
Figure 3:
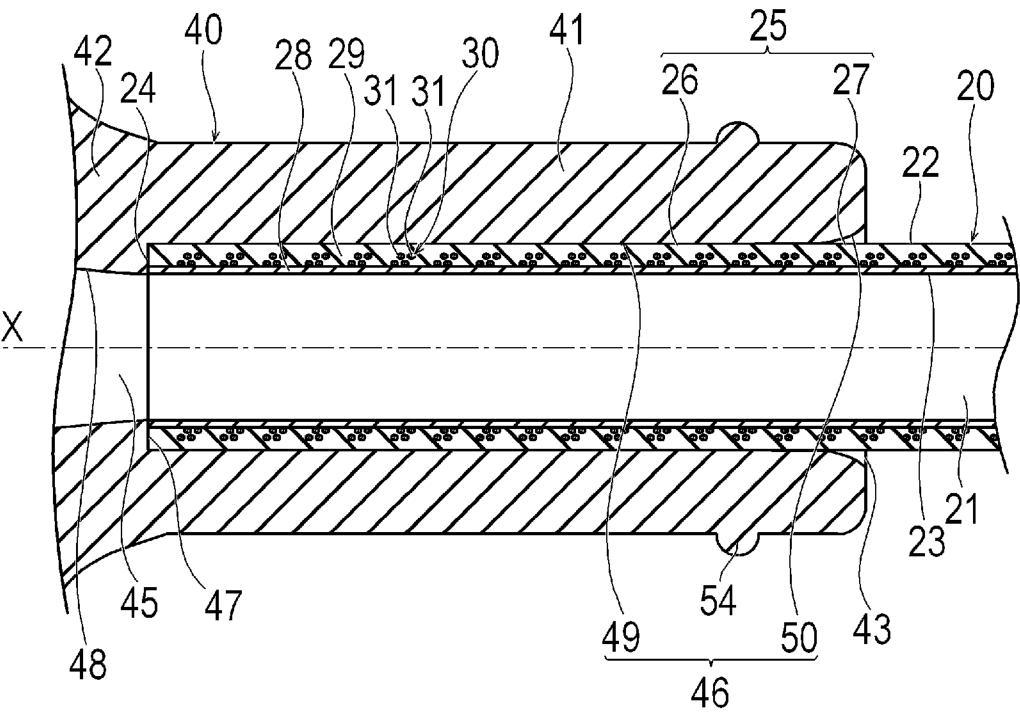
FIG. 3 is a longitudinal cross-sectional view illustrating a distal portion of the hub and the proximal portion of the shaft.

As illustrated in FIGS. 1 to 3, a catheter 10 according to one embodiment disclosed by way example includes a shaft 20 that is an elongated tube or tubular body, a hub 40 fixed to a proximal end of the shaft 20, and a flexible strain relief 60 configured to prevent bending of the shaft 20. In addition to a catheter that supports a guide wire, the catheter 10 may be a guiding catheter, an angiographic catheter, or a microcatheter, or may be a balloon catheter including an inflation lumen or an image diagnosis catheter. In addition, the catheter 10 may be an over-the-wire (OTW) catheter in which a guide wire lumen extending from a distal end of the shaft to the hub is formed, or may be a rapid exchange (RX) catheter in which the guide wire lumen is formed only in a distal portion of the shaft. For example, a guide wire lumen of an RX type balloon catheter may be formed from the distal end of the shaft to an opening portion in the middle in the longitudinal axis direction of the shaft. An inflation lumen through which a fluid for inflating a balloon of the RX type balloon catheter flows may be formed so as to extend from the balloon to a hub at a proximal end of the catheter.

The shaft 20 is formed with a lumen 21 that extends along the shaft 20 from a distal end of the shaft 20 to the proximal end of the shaft 20. The shaft 20 includes a shaft outer surface 22, a shaft inner surface 23 surrounding the lumen 21, and a shaft proximal surface 24 (shaft proximal end surface).

The shaft outer surface 22 is an outer surface of the shaft 20 in a radial direction of the shaft 20, which is a tubular body. The shaft outer surface 22 extends from the distal end of the shaft 20 to the proximal end of the shaft 20. The shaft outer surface 22 includes a shaft proximal side outer surface 25 extending from the proximal end of the shaft 20 toward the distal end of the shaft 20 to a predetermined position along the shaft 20. The shaft proximal side outer surface 25 is surrounded by and accommodated in the hub 40. The shaft proximal side outer surface 25 includes a substantially uniform outer diameter along the longitudinal axis X of the shaft 20. The shaft proximal side outer surface 25 includes a shaft melted surface 26 welded to the hub 40, and a shaft separated surface 27 that is disposed on the distal side of the shaft melted surface 26 and separated from the hub 40. The shaft separated surface 27 is not welded to the hub 40 and is separated (spaced) from the hub 40 with an axial gap therebetween. Thus, the hub 40 axially overlaps a part of the shaft proximal side outer surface 25 to which the hub 40 is welded (i.e., the shaft melted surface 26) and also axially overlaps a part of the shaft proximal side outer surface 25 to which the hub 40 is not welded (i.e., the shaft separated surface 27).

The shaft inner surface 23 is an inner surface of the shaft 20 in the radial direction of the shaft 20, which is a tubular body, and extends from the distal end of the shaft 20 to the proximal end of the shaft 20.

The shaft proximal surface 24 is a surface facing the proximal side or in the proximal direction (to the left in FIGS. 2 and 3) at the proximal end of the shaft 20, and is formed by being cut perpendicularly to the axial center X of the shaft 20.

The shaft 20 in the present embodiment includes an inner layer 28 that forms the shaft inner surface 23, an outer layer 29 that forms the shaft outer surface 22, and a reinforcement body 30 that is embedded in the shaft 20.

In addition to a polyamide resin, a polyester resin, a polyolefin resin and a polyurethane resin, examples of a constituent material from which the outer layer 29 may be fabricated include a polyamide elastomer, a polyester elastomer, a polyurethane elastomer, a mixture of one or more of these examples, and a mixture of materials having different hardnesses. The outer layer 29 may be formed by arranging materials having different hardnesses so as to become softer from the proximal end toward the distal end.

A constituent material from which the inner layer 28 may be fabricated may be the same material as the constituent material of the outer layer 29 described above, or may be a material different from the constituent material of the outer layer 29. The constituent material from which the inner layer 28 may be fabricated may be a fluorine-based resin material such as a polytetrafluoroethylene resin in order to improve sliding property of an inner peripheral surface of the shaft 20.

The reinforcement body 30 reinforces the shaft 20, and is formed by braiding a plurality of reinforcement wires 31 into a tubular shape, with gaps between adjacent wires. In addition, the reinforcement body 30 may also be formed by spirally winding one or more reinforcement wires 31. The material of the outer layer 29 or the inner layer 28 enters gaps between the plurality of reinforcement wires 31 in the reinforcement body 30. The reinforcement wire 31 is made of a metal such as stainless steel or NiTi.

The hub 40 includes a tubular accommodation unit 41 that is disposed on the distal side of the hub 40 and that accommodates a proximal portion of the shaft 20, a hub main body 42 that is disposed on a proximal side of the accommodation unit 41, wings 52, a threading projection 53, and an annular projection 54. In the hub 40, a hub lumen 45 is formed which extends from a hub distal end opening 43 formed at a distal end of the accommodation unit 41 to a hub proximal end opening 44 formed at a proximal end of the hub main body 42. The hub lumen 45 includes an accommodation surface 46 that is an inner peripheral surface of the accommodation unit 41, an adjacent surface 47 that faces the shaft proximal surface 24, and a hub passage 48 that is an inner peripheral surface of the hub main body 42.

The accommodation surface 46 includes a hub melted surface 49 directly welded to the shaft melted surface 26 of the shaft proximal side outer surface 25, and a hub separated surface 50 that is separated outward in the radial direction from the shaft separated surface 27 and faces the shaft separated surface 27. The hub melted surface 49 extends from a proximal end of the accommodation surface 46 toward the distal direction. A proximal end of the hub melted surface 49 is connected to the adjacent surface 47. The hub separated surface 50 extends in the distal direction from a distal end of the hub melted surface 49. As shown in FIG. 3, the hub separated surface 50 is at the distal-most end portion of the tubular accommodation unit and the distal-most end portion of the hub. A gap between the hub separated surface 50 and the shaft proximal side outer surface 25 in the radial direction widens (increases) toward the distal direction. It should be noted that the hub separated surface 50 that forms the gap with the shaft proximal side outer surface 25 may not be provided.

The adjacent surface 47 is an annular surface facing toward the distal side or facing in the distal direction, and is formed substantially perpendicular to the axial center X of the shaft 20. An outer side of the adjacent surface 47 in the radial direction is connected to the hub melted surface 49. An inner side of the adjacent surface 47 in the radial direction is connected to a distal end of the hub passage 48.

The hub passage 48 extends from the adjacent surface 47 in the proximal direction. The hub passage 48 has a tapered shape whose inner diameter gradually increases toward the proximal direction. The hub passage 48 is preferably coaxial with the accommodation surface 46 and further coaxial with the lumen 21. An inner diameter of the distal end of the hub passage 48 is preferably substantially equal to an inner diameter of the shaft 20, but is not limited in this regard. A part of the tapered hub passage 48 may include a Luer tapered portion 51 connectable to a syringe. A guide wire or a treatment catheter inserted from the hub proximal end opening 44 smoothly passes through the hub lumen 45 and the lumen 21 and protrudes from a distal end of the catheter 10. Accordingly, the guide wire and the treatment catheter 10 can easily reach a target position such as a lesion area.

The wings 52 are formed so as to protrude from two opposing locations on an outer peripheral surface of the hub main body 42 such that an operator can easily grip and operate the hub 40. The threading projection 53 is formed on the outer peripheral surface of the hub main body 42 on the proximal side. The threading projection 53 can be engaged with a luer lock type syringe or the like. The annular projection 54 is a projection formed over 360° on an outer peripheral surface of the accommodation unit 41. The annular projection 54 is fittable into a groove formed in an inner peripheral surface of the strain relief 60.

A constituent material from which the hub 40 may be fabricated is not particularly limited as long as the material is a thermoplastic resin that can be injection-molded, a material that easily transmits heat or electromagnetic waves is preferable, and specific examples thereof include a polyolefin resin, a polyamide resin, a polycarbonate resin, and a polyester resin.

Figure 4:
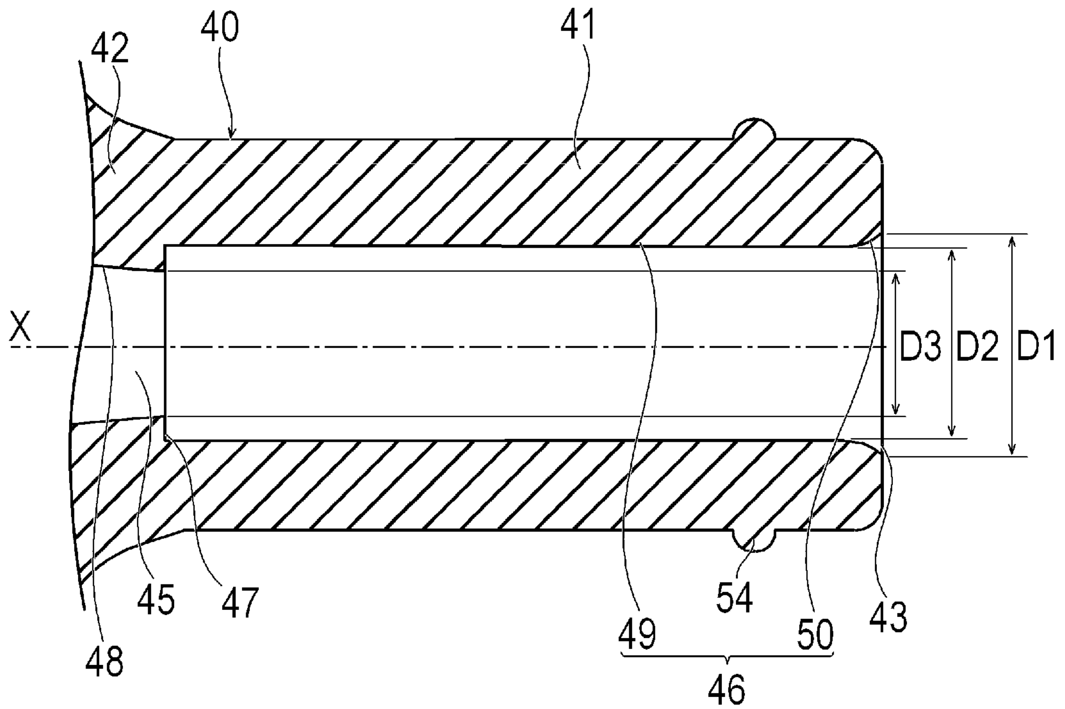
FIG. 4 is a longitudinal cross-sectional view illustrating the distal portion of the hub before the shaft is fixed.

Next, a method of welding the shaft 20 and the hub 40 will be described. As illustrated in FIG. 4, in the hub 40 before the shaft 20 is welded, an inner diameter of the accommodation surface 46 is larger on the distal side than on the proximal side. Specifically, an inner diameter D1 of the hub distal end opening 43 is larger than an inner diameter D2 of the distal end and the proximal end of the hub melted surface 49. In addition, an inner diameter D3 of the distal end of the hub passage 48 is smaller than the inner diameter D2 of the proximal end of the hub melted surface 49. The inner diameter D2 of the hub melted surface 49 is substantially equal to an outer diameter of the shaft proximal side outer surface 25. The inner diameter D1 of the hub distal end opening 43 is, for example, 0.92 mm. The inner diameter D2 of the proximal end of the hub melted surface 49 is, for example, 0.88 mm. The inner diameter D3 of the distal end of the hub passage 48 is, for example, 0.57 mm.

First, the proximal side (proximal portion) of the shaft 20 is inserted into the accommodation unit 41 of the hub 40, and the shaft proximal surface 24 (proximal end surface of the shaft 20) is abutted against the adjacent surface 47. The shaft proximal surface 24 may not be abutted against the adjacent surface 47 and there may be a gap between the shaft proximal surface 24 and the adjacent surface 47. In addition, a proximal end of the shaft proximal side outer surface 25 is abutted against the proximal end of the hub melted surface 49. It should be noted that the shaft proximal side outer surface 25 may not be abutted against the hub melted surface 49, and there may be a gap between the shaft proximal side outer surface 25 and the hub melted surface 49.

Next, a mandrel is inserted into the lumen 21 of the shaft 20, and the shaft proximal side outer surface 25 and the accommodation unit 41 of the hub 40 are heated. Accordingly, the shaft proximal side outer surface 25 and the accommodation surface 46 are melted, and the hub melted surface 49 and the shaft melted surface 26 are welded together. The hub melted surface 49 and the shaft melted surface 26 may have an integrated structure by being mixed with each other. A heating method is not particularly limited, and examples thereof include a method of irradiating electromagnetic waves having a wavelength that allows the electromagnetic waves to be transmitted through the hub 40 and does not allow the electromagnetic waves to be transmitted through the shaft outer surface 22. Since the shaft outer surface 22 does not transmit the electromagnetic waves, the shaft proximal side outer surface 25 is heated and melted at first. Then heat of the shaft proximal side outer surface 25 is transferred to the accommodation unit 41 to melt the accommodation unit 41.

The electromagnetic waves include infrared rays in addition to heat, microwaves, and visible light. The infrared rays are near-infrared rays having a wavelength of about 0.7 μm to 2.5 μm, mid-infrared rays having a wavelength of about 2.5 μm to 4 μm, or far-infrared rays having a wavelength of about 4 μm to 1000 μm, and the infrared rays may be near-infrared rays, mid-infrared rays, far-infrared rays alone or containing two or more types thereof, and may also contain visible light or microwaves.

An electromagnetic wave irradiation method is not particularly limited, and a semiconductor solid-state laser such as a YAG laser using neodymium, a fiber laser, or the like may be used.

The term "electromagnetic waves are transmitted" means that, in addition to being transparent to the naked eye under visible light, a measured transmittance (hereinafter, referred to as the transmittance) is 80% or more, and more preferably 85% or more. The transmittance can be measured by irradiating a sheet having a thickness of 0.4 mm to 0.5 mm prepared by melt-pressing resin pellets with electromagnetic waves having a specific wavelength and using a spectroscopic analyzer, for example, a Fourier transform infrared and near-infrared spectroscopic analyzer. Therefore, since the electromagnetic waves are not limited to visible light, the term "electromagnetic waves are transmitted" includes being transparent with respect to a specific wavelength even if the electromagnetic waves are colored or opaque to the naked eye.

In addition, the term "electromagnetic waves are not transmitted" means that, in addition to being opaque or colored to the naked eye under visible light, the transmittance is less than 80%, preferably less than 10%, and more preferably less than 1%. Therefore, since the electromagnetic waves are not limited to visible light, the term "electromagnetic waves are not transmitted" includes being opaque or absorbed with respect to a specific wavelength even if the electromagnetic waves are transparent to the naked eye.

In the outer layer 29, a pigment that does not transmit heat or electromagnetic waves, or a pigment that absorbs heat or electromagnetic waves, may be mixed in an amount of 0.01 wt % or more and less than 10 wt %, preferably 0.05 wt % or more and 5 wt % or less, and more preferably 0.1 wt % or more and 1 wt % or less with respect to total resin. Alternatively, the outer layer 29 may not contain any pigment, contrast agent, or the like, and the resin forming the outer layer 29 may have a low transmittance with respect to a specific wavelength. Alternatively, in the outer layer 29, a metal having X-ray contrast properties may be mixed in place of, or together with the pigment.

The pigment is not particularly limited as long as the pigment is a pigment that develops white, black, blue, red, or yellow or a mixture thereof, and a black pigment, for example, carbon black is preferable as a pigment that easily absorbs electromagnetic waves. The X-ray contrast agent is, for example, a compound of gold, bismuth, and tungsten, and is more preferably in the form of powder.

Figures 5A, 5B, 6:
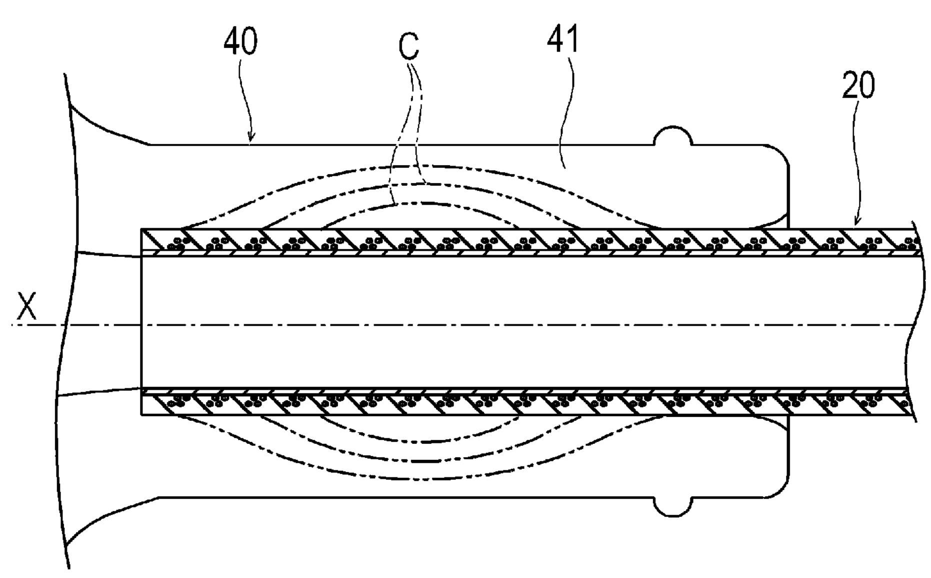

For example, as illustrated in FIG. 5A, when the shaft 20 and the hub 40 are welded to each other by irradiation with an infrared laser L, electromagnetic waves transmitted through the hub 40, which is transparent to a wavelength of the irradiated infrared laser L, are absorbed by the opaque resin, pigment, or the like of the outer layer 29 of the shaft 20 and mainly generate heat. Accordingly, the resin of the outer layer 29 melts and transfers heat H to the accommodation unit 41 of the hub 40, and at least a part of the accommodation surface 46 melts. As illustrated in FIG. 5B, a diameter (inner diameter) of the melted accommodation surface 46 decreases, and the accommodation surface 46 is brought into close contact with the shaft proximal side outer surface 25, and is welded to the shaft proximal side outer surface 25. Accordingly, the hub melted surface 49 and the shaft melted surface 26 are welded and formed. At this time, the accommodation surface 46 melts and the diameter thereof decreases, but the outer peripheral surface of the accommodation unit 41 hardly melts and hardly deforms since heat is hardly transmitted. Therefore, due to the diameter decrease of the accommodation surface 46, the material constituting the accommodation surface 46 flows so as to fill a gap between the accommodation surface 46 and the shaft proximal side outer surface 25, and as a result, a length of the accommodation unit 41 along the axial center X (axial length of the accommodation unit 41) is reduced. Accordingly, the accommodation unit 41 and the shaft proximal side outer surface 25 are favorably welded to each other without any gap therebetween. In addition, the shaft proximal surface 24 and the adjacent surface (facing surface) 47 are also melted and welded by the heat generation of the outer layer 29. It should be noted that the shaft proximal surface 24 may not be welded to the adjacent surface 47.

As illustrated in FIG. 3, the hub separated surface 50 located at the distal end of the hub melted surface 49 is not welded to the shaft separated surface 27, and a gap is maintained between the hub separated surface 50 and the shaft separated surface 27. When the entire hub melted surface 49 located on the proximal side of the hub separated surface 50 is welded to the shaft melted surface 26, the irradiation of the infrared laser L is stopped. Accordingly, fixation of the hub 40 and the shaft 20 is completed. When the melted material is cooled and solidified, residual strain remains on the hub 40 as illustrated in FIG. 6. The residual strain can be measured by an X-ray residual stress measurement device, a two-dimensional birefringence measurement device, or the like. In a cross-section passing through the axial center X, contour lines C drawn by connecting points of the same residual strain of the hub 40 are formed in arc shapes protruding outward in the radial direction, as illustrated in FIG. 6. That is, an absolute value of the residual strain is large at substantially a center in a direction along the axial center X of in a range where the accommodation unit 41 is welded, decreases outward in the radial direction, and decreases toward the distal direction and the proximal direction along the axial center X. In other words, the contour lines C are formed in shapes approximate to a part of an arc of an ellipse having a major axis extending along the axial center X. In a three-dimensional shape of the hub 40, a constant height surface formed by connecting the points of the same residual strain of the hub 40 is formed in a shape approximate to a part of an outer peripheral surface of a rotational ellipsoid having a major axis extending along the axial center X.

As described above, the catheter 10 according to the present embodiment includes: the shaft 20 that is the tubular body in which the lumen 21 extending the shaft 20 from the distal end to the proximal end is formed, and that includes the shaft proximal surface 24 in which the lumen 21 is opened and the shaft outer surface 22 that is the outer peripheral surface of the tubular body; and the hub 40 attached to the proximal end of the shaft 20. The hub 40 includes the tubular accommodation unit 41 configured to accommodate the shaft 20, the accommodation unit 41 includes the hub melted surface 49 directly welded to the shaft outer surface 22, and the absolute value of the residual strain of the accommodation unit 41 decreases from the hub melted surface 49 outward in the radial direction.

In the catheter 10 configured as described above, since the absolute value of the residual strain of the accommodation unit 41 caused by welding decreases from the hub melted surface 49 outward in the radial direction, the shaft 20 and the hub 40 can be firmly fixed and firmly welded, and thus a decrease in dimensional accuracy of an outer side of the hub 40 in the radial direction can be prevented. Therefore, the shaft 20 can be prevented from being detached from the hub 40 in a case where a high pressure of a contrast agent injected into the catheter 10 is applied, a case where a tensile force acts between the hub 40 and the shaft 20 when the shaft 20 is pulled out from a body, or the like. Further, since a dimensional change on an outer side in the radial direction of the accommodation unit 41 can be reduced, it is easy to attach components such as the strain relief 60 to the outer side of the accommodation unit 41. In addition, when a compression residual strain decreases from the hub melted surface 49 outward in the radial direction, a force for fixing the hub 40 to the shaft 20 can be increased.

In addition, the contour line C of the absolute value of the residual strain of the accommodation unit 41 in the cross section passing through the axial center of the accommodation unit 41 is formed in the arc shape protruding outward in the radial direction. Accordingly, the absolute value of the residual strain gradually decreases from a portion of the hub melted surface 49 where the absolute value is largest toward two directions, namely the outer side in the radial direction and the axial center direction (the distal direction and the proximal direction). Therefore, occurrence of shape distortion of the accommodation unit 41 can be effectively prevented.

In addition, the shaft proximal surface 24 is welded to the hub 40. Accordingly, the shaft 20 and the hub 40 can be fixed more firmly.

In addition, the hub separated surface 50 that is separated outward in the radial direction from the shaft outer surface 22 and faces the shaft outer surface 22 is formed on the distal side of the accommodation unit 41. Accordingly, since the shaft 20 is easily bent on an inner side of the distal end of the accommodation unit 41, stress concentration on the shaft 20 can be prevented, and damage to the shaft 20 can be prevented. In addition, since the shaft 20 is easily bent on the inner side of the distal end of the accommodation unit 41, when the shaft 20 is bent, it is possible to prevent a force that peels off the shaft 20 from the hub melted surface 49 of the accommodation unit 41 from acting thereon, and thus the fixation of the shaft 20 and the hub 40 can be effectively maintained.

The present invention is not limited to the above-described embodiment, and various modifications can be made by those skilled in the art within the technical idea of the present invention. For example, the shaft 20 may be heated by high-frequency induction heating during which heating is performed by electromagnetic induction. An electromagnetically-induced conductor is, for example, the reinforcement body 30.

The detailed description above describes embodiments of a catheter and method of making a catheter representing examples of the inventive catheter and manufacturing method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE SIGNS LIST

10 catheter
20 shaft
21 lumen
22 shaft outer surface
23 shaft inner surface
24 shaft proximal surface
25 shaft proximal side outer surface
26 shaft melted surface
27 shaft separated surface
28 inner layer
29 outer layer
30 reinforcement body
40 hub
41 accommodation unit
42 hub main body
43 hub distal end opening
44 hub proximal end opening
45 hub lumen
46 accommodation surface
47 adjacent surface
48 hub passage
49 hub melted surface
50 hub separated surface
60 strain relief

What is claimed is:

1. A catheter comprising:

a shaft possessing a distal end and a proximal end, the shaft being a tubular body that includes a lumen extending from the distal end of the shaft to the proximal end of the shaft, the shaft including a shaft proximal end surface at the proximal end of the shaft, the lumen opening to the shaft proximal end surface at the proximal end of the shaft, the shaft also possessing a shaft outer surface that is an outer peripheral surface of the tubular body;

a hub attached to the proximal end of the shaft;

the hub including a tubular accommodation unit in which is accommodated a portion of the shaft;

the accommodation unit including a hub melted surface that is directly welded to the shaft outer surface so that the accommodation unit is welded to the shaft outer surface at a welded surface;

an absolute value of a residual strain of the accommodation unit decreases outward in a radial direction from the welded surface; and the accommodation unit of the hub including a longitudinal axis, and a contour line of the absolute value of the residual strain of the accommodation unit in a cross section passing through the longitudinal axis of the accommodation unit is arc-shaped protruding outward in the radial direction.

2. The catheter according to claim 1, wherein the shaft proximal surface is welded to the accommodation unit of the hub.

3. The catheter according to claim 1, wherein a hub separated surface that is separated outward in the radial direction from the shaft outer surface and faces the shaft outer surface is provided on a distal side of the accommodation unit.

4. The catheter according to claim 1, wherein the hub includes a hub lumen that extends throughout the hub from a distal end of the hub to a proximal end of the hub, the hub lumen including a distal portion and a proximal portion, the portion of the shaft being accommodated in the distal portion of the hub lumen, at least an axially extending part of the proximal portion of the hub lumen possessing a tapered shape gradually increasing toward the proximal end of the hub.

5. The catheter according to claim 1, wherein the hub includes a hub lumen that extends throughout the hub from a distal end of the hub to a proximal end of the hub, the hub lumen including a distal portion in which is accommodated the portion of the shaft, the shaft including an axially facing shaft proximal end surface at a proximal end of the shaft, the shaft proximal end surface facing and being in contact with an adjacent surface in the distal portion of the hub lumen, a portion of the hub lumen immediately proximal of the adjacent surface being tapered so as to gradually increase in a direction away from the shaft proximal end surface.

6. The catheter according to claim 1, wherein the shaft includes a reinforcement body embedded in the shaft.

7. The catheter according to claim 6, wherein the reinforcement body is comprised of wires that are braided or spirally wound, with gaps between adjacent wire portions, the shaft being made of a material positioned in the gaps.

8. The catheter according to claim 1, wherein the tubular accommodation unit possesses a distal-most end portion that is distal of the welded surface, an inner surface of the tubular accommodation unit facing the shaft outer surface, the inner surface of the tubular accommodation unit being spaced from the shaft outer surface so that a gap exists between the inner surface of the tubular accommodation unit and the shaft outer surface.

9. A catheter comprising:

a shaft possessing a distal end and a proximal end, the shaft being a tubular body that includes a lumen extending from the distal end of the shaft to the proximal end of the shaft, the shaft including a shaft proximal end surface at the proximal end of the shaft, the lumen opening to the shaft proximal end surface at the proximal end of the shaft, the shaft also possessing a radially outwardly facing shaft outer surface that extends from the distal end of the shaft toward the proximal end of the shaft and that terminates at the shaft proximal end surface;

the shaft including a proximal portion, the proximal portion of the shaft including a radially outer portion and a radially inner portion that both extend along an axial extent of the proximal portion of the shaft, the radially inner portion of the proximal portion of the shaft being radially inward of the radially outer portion of the proximal portion of the shaft;

a hub including an accommodation unit in which is positioned the proximal portion of the shaft;

the radially outer portion of the proximal portion of the shaft being comprised of a resin that absorbs electromagnetic waves or does not transmit electromagnetic waves so that the outer surface of the proximal portion of the shaft that is accommodated in the accommodation unit is heated and melted when irradiated with electromagnetic waves;

the accommodation unit including a hub melted surface that is directly welded to the shaft outer surface of the proximal portion of the shaft so that the accommodation unit and the shaft outer surface are welded to one another; and the accommodation unit including a distal-most portion possessing an inner surface that faces the radially outwardly facing shaft outer surface and is spaced from and not welded to the radially outwardly facing shaft outer surface so that a gap exists between the inner surface of the accommodation unit and the radially outwardly facing shaft outer surface that face one another.

10. The catheter according to claim 9, wherein the accommodation unit and the shaft outer surface are welded to one another at a welded surface and a residual strain is present in the accommodation unit, the accommodation unit of the hub including a longitudinal axis, and a contour line of the absolute value of the residual strain of the accommodation unit in a cross section passing through the longitudinal axis of the accommodation unit being arc-shaped protruding outward in the radial direction.

11. The catheter according to claim 9, wherein the resin of the radially outer portion is a resin containing pigment that absorbs or does not transmit the electromagnetic waves so that the radially outer portion of the shaft is heated and melts when the accommodation unit is irradiated with an infrared laser.

12. The catheter according to claim 9, wherein an absolute value of a residual strain of the accommodation unit decreases in a radially outward direction from the welded surface.

13. The catheter according to claim 9, wherein an absolute value of a residual strain of the accommodation unit gradually decreases, from a portion of the hub melted surface at which the absolute value is largest, toward both a distal direction and a proximal direction.

14. The catheter according to claim 9, wherein the accommodation unit of the hub is comprised of thermoplastic resin that is transparent to the electromagnetic waves.

15. The catheter according to claim 9, wherein the shaft proximal end surface at the proximal end of the shaft faces an adjacent surface of the accommodation unit of the hub, the hub including a hub passage that extends from the adjacent surface to a proximal end of the hub, the hub passage communicating with the lumen in the shaft.

16. The catheter according to claim 15, wherein at least an axially extending part of the hub passage possesses a tapered shape gradually increasing toward the proximal end of the hub.

17. The catheter according to claim 15, wherein the gap between the inner surface of the accommodation unit and the shaft outer surface gradually widens toward a distal direction.

18. The catheter according to claim 9, wherein the shaft includes a reinforcement body embedded in the shaft, the reinforcement body being comprised of wires that are braided or spirally wound, with gaps between adjacent wire portions, the shaft being made of a material positioned in the gaps.

19. A method of securing a shaft of a catheter to a hub of the catheter, the method comprising:

positioning a proximal portion of the shaft in an accommodation unit of the hub, the accommodation unit of the hub being a distal portion of the hub, the accommodation unit of the hub possessing an inner surface and a distal end portion, the proximal portion of the shaft possessing a shaft outer surface, the positioning of the proximal portion of the shaft in the accommodation unit of the hub comprising positioning the proximal portion of the shaft in the accommodation unit of the hub so that the inner surface of the accommodation unit of the hub faces the shaft outer surface of the proximal portion of the shaft, the proximal portion of the shaft that is positioned in the accommodation unit of the hub being made of a material that does not transmit heat or electromagnetic waves or that absorbs heat or electromagnetic waves, the accommodation unit of the hub in which the proximal portion of the shaft is positioned being made of a material that transmits heat or electromagnetic waves;

irradiating electromagnetic waves having a wavelength that allows the electromagnetic waves to be transmitted through the accommodation unit of the hub in which the proximal portion of the shaft is positioned and that does not allow the electromagnetic waves to be transmitted through the shaft outer surface heating the shaft outer surface of the proximal portion of the shaft so that the shaft outer surface of the proximal portion of the shaft is heated and melted;

transferring the heat of the shaft outer surface of the proximal portion of the shaft to the inner surface of the accommodation unit to melt at least a part of the inner surface of the accommodation unit to weld the part of the inner surface of the accommodation unit and the shaft proximal side outer surface at a welded surface;

an absolute value of a residual strain of the accommodation unit of the hub decreases outward in a radial direction from the welded surface.

20. The method according to claim 19, wherein the heating of the shaft outer surface of the proximal portion of the shaft comprises transmitting electromagnetic waves through the accommodation unit of the hub so that the electromagnetic waves do not heat the accommodation unit of the hub, and absorbing the electromagnetic waves in the proximal portion of the shaft.

21. The method according to claim 19, wherein the accommodation unit of the hub includes a longitudinal axis, and a contour line of the absolute value of the residual strain of the accommodation unit in a cross section passing through the longitudinal axis of the accommodation unit is arc-shaped, protruding outward in the radial direction.

* * * * *